(12) United States Patent
Carriazo

(10) Patent No.: US 6,818,004 B2
(45) Date of Patent: Nov. 16, 2004

(54) ASPHERICAL POSITIONING RING

(76) Inventor: Cesar C. Carriazo, Calle 86 No. 49C 69, Baranquilla (CO)

( * ) Notice: Subject to any disclaimer, the term of this patent is extended or adjusted under 35 U.S.C. 154(b) by 34 days.

(21) Appl. No.: 10/002,639

(22) Filed: Oct. 24, 2001

(65) Prior Publication Data

US 2003/0078607 A1 Apr. 24, 2003

(51) Int. Cl.[7] .................................................. A61F 9/00
(52) U.S. Cl. ....................................................... 606/166
(58) Field of Search ................................ 606/166, 4, 5, 606/6, 107; 601/113; 623/5.11, 5.12, 6.12, 6.23, 907, 6.24

(56) References Cited

U.S. PATENT DOCUMENTS

| | | | |
|---|---|---|---|
| 5,011,498 A | 4/1991 | Krumeich et al. | |
| 5,395,385 A | 3/1995 | Kilmer et al. | |
| 5,496,339 A | 3/1996 | Koepnick | |
| 5,549,632 A | 8/1996 | Lai | |
| 5,586,980 A | 12/1996 | Kremer et al. | |
| RE35,421 E | 1/1997 | Ruiz et al. | |
| 5,980,543 A | 11/1999 | Carriazo et al. | |
| 6,007,553 A | * 12/1999 | Hellenkamp et al. | 606/166 |
| 6,030,398 A | * 2/2000 | Klopotek | 606/166 |
| 6,071,293 A | 6/2000 | Krumeich | |
| 6,126,668 A | 10/2000 | Bair et al. | |
| 6,143,010 A | 11/2000 | Silvestrini et al. | |
| 6,165,189 A | 12/2000 | Ziemer | |
| 6,197,038 B1 | 3/2001 | O'Donnell | |
| 6,296,650 B1 | 10/2001 | Carriazo | |
| 6,350,272 B1 | * 2/2002 | Kawesch | 606/166 |
| 6,506,198 B1 | * 1/2003 | Amano | 606/166 |
| 2003/0045895 A1 | * 3/2003 | Ross et al. | 606/166 |

* cited by examiner

Primary Examiner—David O. Reip
Assistant Examiner—D. Jacob Davis
(74) Attorney, Agent, or Firm—Streets & Steele; Jeffrey L. Streets; Steven L. Christian

(57) ABSTRACT

A suction ring providing an inferior engaging surface and a superior engaging surface that engages and grips the ocular globe, immobilizing the ocular globe relative to a corneal surgical procedure. The inferior engaging surface grips the sclera of the ocular globe while the superior engaging surface grips the corneal region. The suction ring also provides an aperture sized to receive and expose the cornea for a surgical procedure.

The suction ring has a non-circular gripping structure to provide a closer fit to abnormally shaped ocular globes and corneas. The aperture is non-circular to enable the surgeon to obtain a non-circular corneal disk during a lamellar keratotomy procedure.

32 Claims, 10 Drawing Sheets

ASPHERICAL POSITIONING RING

FIELD OF THE INVENTION

This invention relates to surgical apparatus and methods for performing lamellar keratotomies. More particularly, the invention relates to a positioning ring for temporarily immobilizing the eyeball, or ocular globe, such that the globe's cornea protrudes therethrough.

BACKGROUND OF THE RELATED ART

In a normal eye, parallel rays of light entering the eye become focused on the retina to create a sharp visual image. Anomalies in the overall shape of the eye, however, may result in image distortion by causing parallel rays of light entering the eye to become focused at a location other than the retina. Hyperopia, or farsightedness, occurs when the front-to-back measurement of the eyeball is too short, causing parallel rays of light entering the eye to focus behind the retina. In contrast, myopia, or nearsightedness, occurs when the front-to-back measurement of the eyeball is too long, causing parallel rays of light entering the eye to focus in front of the retina. Astigmatism occurs when the parallel rays of light entering the eye do not focus at a single point in the eye, but rather have a variable focus due to an aspherical cornea refracting light in a different meridian at different distances.

Glasses or contact lenses usually correct hyperopia, myopia and astigmatism but surgical corrective methods have become quite popular due to the inconvenience and discomfort of wearing glasses or contact lenses. One of these surgical corrective methods is laser-assisted in-situ keratomileusis (LASIK). During the LASIK procedure, a microkeratome is used to perform an incomplete lamellar keratotomy, which leaves a peripheral residue of corneal tissue uncut to act as a hinge. The hinge permits the corneal disk to be lifted for exposing and resecting the stromal layer with a laser. The tissue removed by the laser reshapes the stromal layer so that the stromal layer will sufficiently refract the light rays entering the eye to cause them to focus on the retina, producing a sharp visual image without the aid of glasses or contact lenses. After the laser completes the reshaping of the stromal layer, the corneal disk is folded back into its original position, using the hinge as a guide. Within minutes, the corneal disk adheres itself to the rest of the cornea and the LASIK procedure is complete.

There are many different designs for microkeratomes but certain aspects of their operation are similar. A suction ring is first affixed to the sclera and centered about the cornea so that the cornea extends through an aperture and above the suction ring. The diameter of the aperture in the suction ring through which the cornea extends is selected on the basis of the size of the cornea and the diameter of the corneal disk to be cut. The suction ring is held to the sclera by a vacuum induced in the area between the cylindrical ring and the eyeball. A float head having a flat, arcuate or oblique surface is then moved over the guide ring so as to compress the cornea into a shape that complements the surface. A cutting head carrying a blade is then moved across the suction ring so as to resect a corneal disk. The float head may be held stationary once it has compressed the cornea prior to the movement of the blade, or the float head may be moved with the blade head while maintaining contact with the cornea. The cutting blade is moved a predetermined distance substantially, but not completely, across the portion of the cutting plane that intersects the cornea. The movement of the cutting blade is restricted by an adjustable stop means, whereby the extent of hinge width formed on the corneal disk is adjustable. The cutting blade is then moved back across the suction ring to its original position, so that the suction ring can be removed and the resulting corneal disk can be folded back and secured over its hinge, exposing the corneal stroma to be reshaped by the laser.

While the use of the hinge has made corrective surgery easier and safer by helping to ensure that the corneal disk is replaced in its original position, the hinge has the disadvantage that it can potentially block a section of the ablation zone covered by the corneal disk hinge. FIG. 1 shows a plan view of an ocular globe (eyeball) with the corneal disk 11 folded back over the hinge 14, exposing the stromal layer 12 and the laser ablation zone 13 after an incomplete lamellar keratotomy. For a corneal disk cut with the existing microkeratomes, only about 60% to 70% of the circle diameter of the corneal disk may be safely used because of the interference caused by the hinge. In the example shown in FIG. 1, a 10 mm diameter corneal disk 11 is cut and folded back over the hinge 14. The resulting laser ablation zone 13 has a diameter of only 6 mm because the hinge area plus a safety zone required to protect against laser damage to the hinge, is 2 mm wide and, because both the corneal disk 11 and the laser ablation zone 13 are circles, the same 2 mm of the diameter in the counter-lateral quadrant, or the opposing quadrant furthest from the center of the eye, cannot be used for a circular laser ablation. Therefore, in this example, of the original 10 mm diameter, only 6 mm can be used for laser ablation.

Using a smaller suction ring aperture diameter to reduce the diameter of the corneal disk may be especially harmful if the stromal zone exposed by the microkeratome is smaller than the laser ablation zone, as then ablation may occur over the hinge. This type of ablation damage, referred to as negative hinge syndrome, creates or produces an irregularity of the ablation with an inevitable astigmatic induction, loss of visual acuity, and a decrease in contrast sensibility.

To prevent negative hinge syndrome, surgeons performing LASIK will either obtain unnecessarily large corneal disks or move the suction ring toward the position where the hinge will be located to gain more stromal tissue exposure for the ablation. Obtaining unnecessarily large corneal disks increases the risk of complications from the higher vacuum required under the suction ring to hold the larger suction ring in place on the sclera during the incomplete lamellar keratotomy procedure. Using the higher vacuum increases the intraocular pressure, thereby placing eye structures, such as the retina, at risk. Moving the suction ring toward the position where the hinge will be located to gain more stromal tissue exposure creates a change in the anatomical coupling of the eye with the ring, therefore increasing the risks of suction loss and serious corneal damage during the incomplete lamellar keratotomy procedure.

The suction ring must be securely affixed to the sclera and the corneal region by the suction induced by a vacuum pump. On some eyes, the eyeball is aspherical to a larger degree than normal making it difficult to achieve a good suction seal between the sclera and the suction ring. A cornea with a higher degree of astigmatism will also make it more difficult to seal the corneal region against the aperture on the top end of the suction ring. The suction ring is a cylinder with a circular aperture on the top end through which the cornea is exposed for cutting. The bottom end of the suction ring is also circular and attaches to the sclera by suction induced by a vacuum, normally pulled through ports around the inside wall of the suction ring. A small vacuum pump is used to create the vacuum. To acquire the necessary suction to hold the suction ring in place on the eye, a seal must be maintained both around the bottom end of the suction ring with the sclera as well as the top aperture of the suction ring with the corneal region. This is illustrated in FIGS. 2, 3 and 4.

FIG. 2 shows a properly fitted suction ring on an eye. A good suction seal is formed between the corneal region and the top aperture 25 and the sclera and the bottom end of the suction ring 24. The suction chamber 21 is the volume inside the cylinder formed by the suction ring and sealed by the eye. The vacuum is induced through port 22 to the vacuum pump.

FIGS. 3 A–B show a poorly fitting suction ring at the top aperture. In this example, the cornea is misshapen due to astigmatism such that the suction ring, in FIG. 3A, does not adequately seal between the corneal region and the top aperture 25 along the a–a' meridian. However, in FIG. 3B, the suction ring is well sealed between the corneal region and the top aperture 25 along the b–b' meridian. FIGS. 4 A–B show a poorly fitting suction ring at the bottom end of the suction ring. In this example, the eyeball is aspherical causing, as shown in FIG. 4A, a poor suction seal between the sclera and the bottom end of the suction ring 24 along the a–a' meridian. However, in FIG. 4B, the suction ring is well sealed between the sclera and the bottom end of the suction ring 24 along the b–b' meridian.

The majority of refractive surgery cases have an astigmatic cornea of less than 2 diopters between one meridian and the other. When the cornea is extended into the top aperture of the suction ring, the flatter meridian tends to curve and the more curved meridian tends to flatten to conform to the suction ring. The suction produced by the vacuum pump helps the cornea to adjust and fit into the aperture. However, when the astigmatic cornea is greater than 2 diopters between one meridian and the other, or the difference in radii between one meridian and the other is greater than about 1 mm, the risk of losing the suction seal when the cornea is flattened and pushed downwards with the float head increases and, if greater vacuum is used to seal the suction chamber, the structures of the eye are at risk as the intraocular pressure increases. Thus, as the cornea's astigmatism increases, the risk of having suction problems during the procedure also increases.

Therefore there is a need for a suction ring shaped in such a way as to ensure a good suction seal both around the top aperture for an astigmatic cornea as well as a good suction seal around the sclera for an aspherical eyeball. It would be very advantageous to have a microkeratome that greatly reduced the risk of suction loss between the eyeball and the suction ring while performing an incomplete lamellar keratotomy procedure. It would be desirable to have a device for performing an incomplete lamellar keratotomy that would produce a hinge that does not occlude a large area from the laser ablation area.

SUMMARY OF THE INVENTION

The present invention provides a suction ring for immobilizing an ocular globe during a surgical procedure on the cornea. The suction ring provides an inferior engaging surface and a superior engaging surface that engages and grips the ocular globe, immobilizing the ocular globe relative to the surgical procedure. The inferior engaging surface grips or engages the sclera of the ocular globe while the superior engaging surface grips or engages the corneal region. The engaged corneal region is the cornea and one portion of the limbo, the zone that joins the cornea and the conjunctiva. The suction ring also provides an aperture sized to receive and expose the cornea for a surgical procedure.

The inferior and superior engaging surfaces are secured against the ocular globe by suction induced by a slight vacuum pulled by a vacuum pump or other vacuum source. Between the inferior and superior engaging surfaces is an annular vacuum channel that is connected to the vacuum pump via a tube. When suction is applied by pulling a slight vacuum, the ocular globe is slightly pulled into the channel between the inferior and superior engaging surfaces, resulting in the eye being "pinched" and securely held in place relative to the suction ring for the surgical procedure.

The present invention is a suction ring used for a lamellar keratotomy during LASIK refractive correction. The suction ring has a shape more easily adapted to aspherical ocular globes and astigmatic corneas. The suction ring immobilizes the ocular globe in relation to the microkeratome by gripping the sclera and corneal region through suction imposed by a vacuum pump. It is vitally important that the suction grip be maintained during the lamellar keratotomy to prevent the blade on the microkeratome from accidentally cutting into unintended structures of the eye and severely damaging them. When a cornea has an abnormal amount of astigmatism or an ocular globe is abnormally aspherical or ellipsoidal, the risk of suction loss during the lamellar keratotomy increases because the circular suction rings currently used do not have a sufficiently close fit to these shapes to form a reliable suction seal needed to grip the sclera and corneal region. The present invention uses a suction ring having a gripping structure that provides a closer fit to abnormally shaped ocular globes and corneas.

The present invention also provides non-circular apertures for receiving and exposing the cornea for the surgical procedure. The non-circular aperture enables the surgeon to obtain a non-circular corneal disk during the lamellar keratotomy procedure with a microkeratome using a horizontal cutting movement across the cornea.

The present invention also provides a microkeratome, used for performing a lamellar keratotomy, with the suction ring of the present invention.

BRIEF DESCRIPTION OF THE DRAWINGS

So that the above recited features and advantages of the present invention can be understood in detail, a more particular description of the invention, briefly summarized above, may be had by reference to the embodiments thereof that are illustrated in the appended drawings. It is to be noted, however, that the appended drawings illustrate only typical embodiments of this invention and are therefore not to be considered limiting of its scope, for the invention may admit to other equally effective embodiments.

FIGS. 8A 1–2 are a cross-sectional side view of suction ring providing non-circular inferior and superior engaging beveled surfaces.

FIGS. 8B 1–2 are a cross-sectional side view of a suction ring providing a non-circular superior engaging surface with no beveling.

FIGS. 8C 1–2 are a cross-sectional side view of a suction ring providing a non-circular inferior engaging surface with no beveling.

FIGS. 8D 1–2 are a cross-sectional view of a suction ring providing non-circular superior and inferior engaging surfaces by varying the height of the suction chamber.

DETAILED DESCRIPTION OF THE INVENTION

The present invention provides a suction ring for use with a microkeratome during an incomplete lamellar keratotomy procedure. This lamellar keratotomy procedure is used during laser-assisted in-situ keratomileusis (LASIK) surgery to correct refractive qualities of the eye. During the LASIK procedure, a microkeratome is used to perform an incomplete lamellar keratotomy, which leaves a peripheral residue of corneal tissue uncut to act as a hinge. The hinge permits the corneal disk to be lifted for exposure of the stromal layer to be resected with a laser. The tissue removed by the laser reshapes the stromal layer so that the stromal layer will sufficiently refract the light rays entering the eye to cause them to focus on the retina, producing a sharp visual image without the aid of glasses or contact lenses. Alternatively, the present invention could be used for any procedure that involves immobilizing the ocular globe (eyeball) in relation to surgical tools for a surgical procedure on the cornea.

Figure 1:
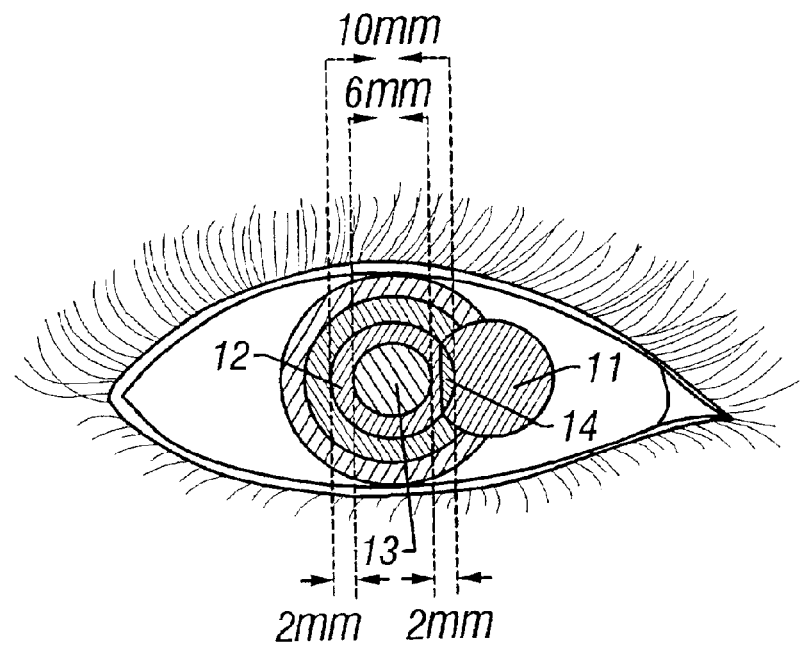
FIG. 1 is a plan view of an ocular globe with a corneal disk folded back over its hinge.
Figure 2:
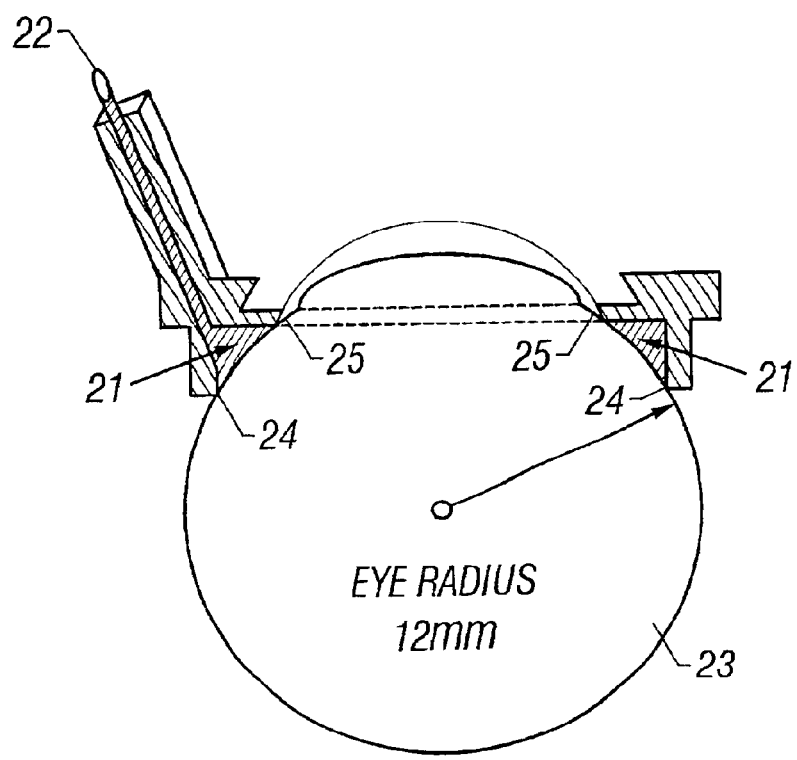
FIG. 2 is a cross-sectional side view of a properly fitted suction ring to the ocular globe.
Figure 3A:
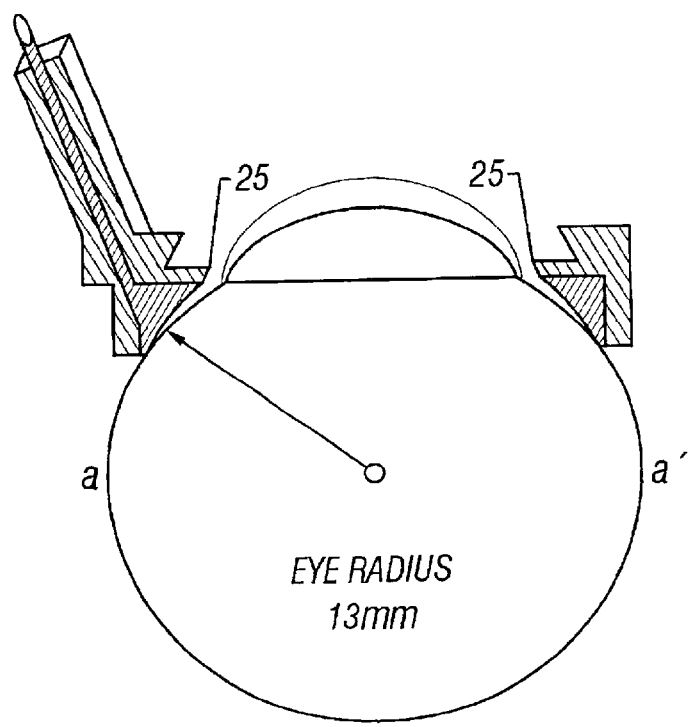
FIGS. 3 A–B are a cross-sectional side view of an improperly fitted suction ring to the ocular globe at the top aperture.
Figure 3B:
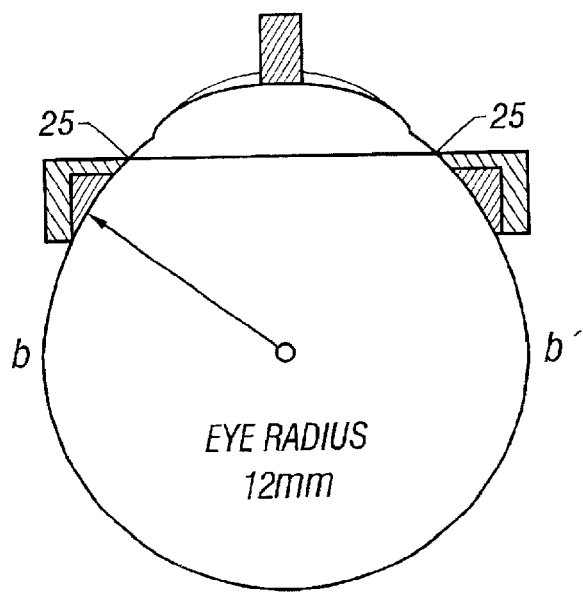
Figure 4A:
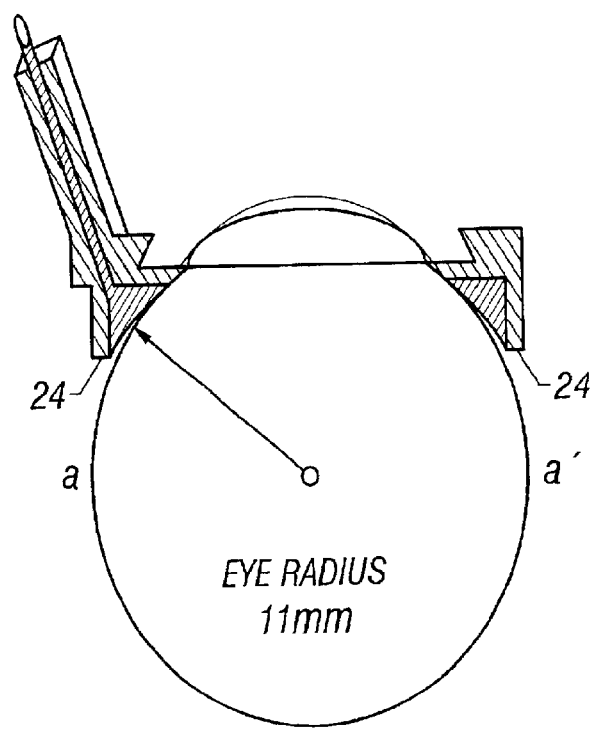
FIGS. 4 A–B are a cross-sectional side view of an improperly fitted suction ring to the ocular globe at the bottom aperture.
Figure 4B:
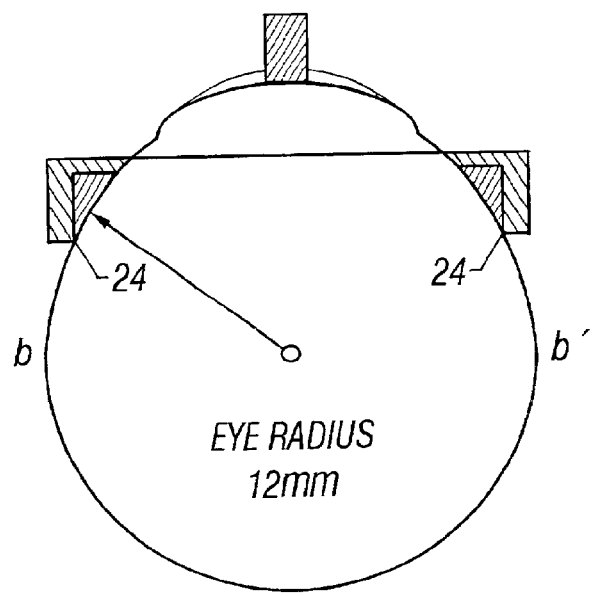
Figure 5A:
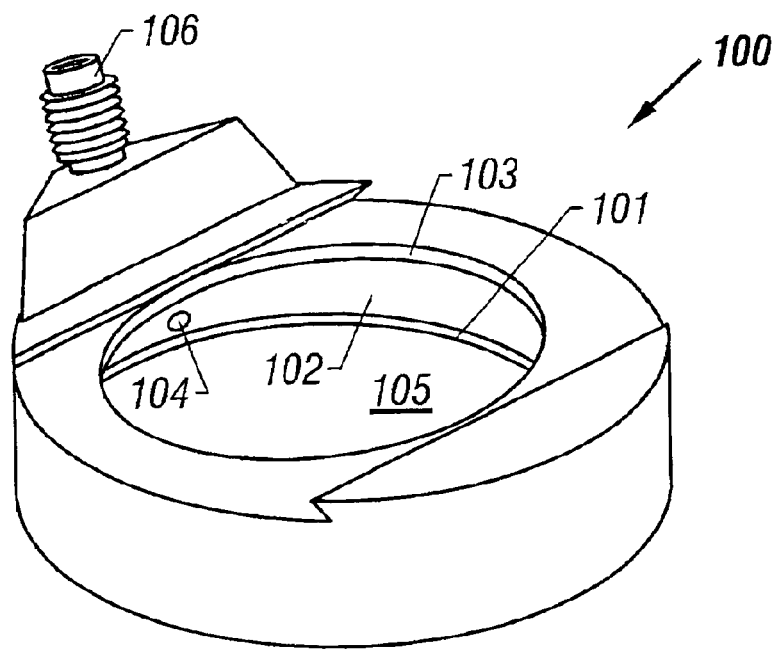
FIGS. 5 A–B presents a perspective view of an oval and a circular suction ring.
Figure 5B:
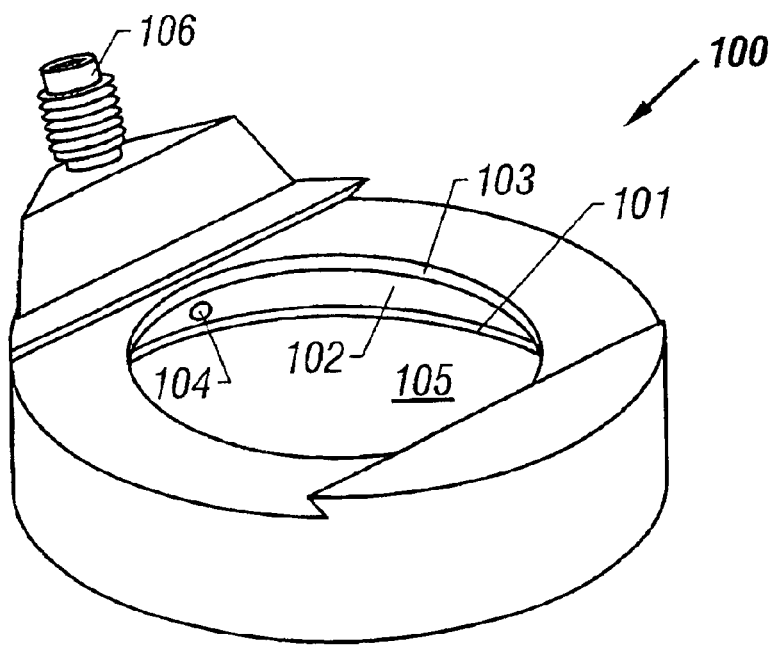
Figure 6:
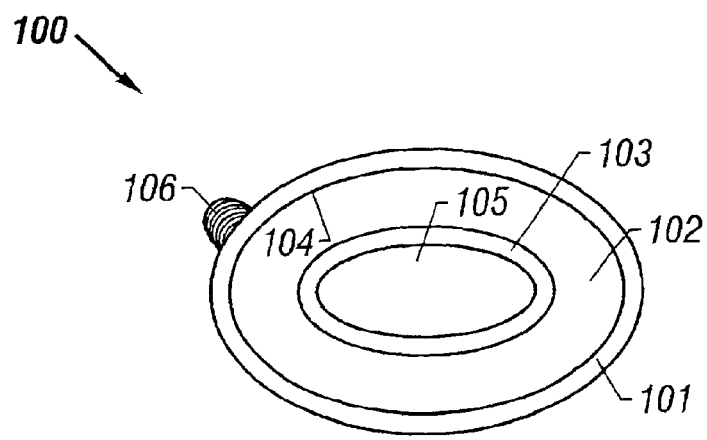
FIG. 6 provides a bottom view of the suction ring.
Figure 7A:
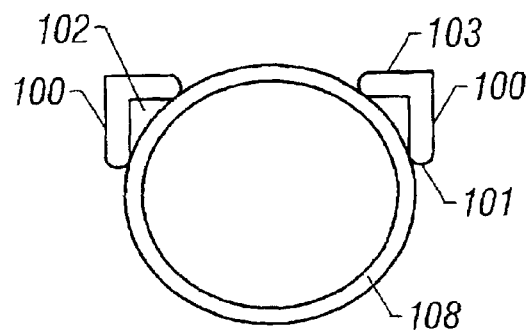
FIG. 7A is a cross-sectional side view of a suction ring on an ocular globe.
Figure 7B:
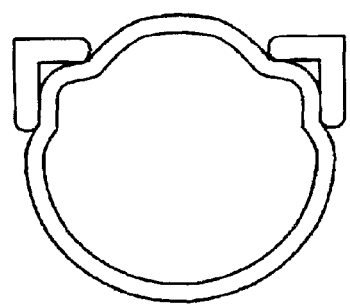
FIG. 7B is a cross-sectional side view of a suction ring on an ocular globe with the effect of the suction on the ocular globe.

FIG. 5A presents a perspective view and FIG. 6 presents a bottom view of the oval suction ring of the present invention. FIG. 5B presents a perspective view of the circular suction ring of the present invention. The suction ring 100 presents an aperture 105 into which the cornea is received. A tube connection 106 is used to connect the suction ring through a tube to a vacuum source, such as a vacuum pump not shown, to provide suction through a suction port 104 in the annular vacuum channel 102. The inferior engaging surface 101, which is the inferior inner wall of the suction ring, is placed on the sclera and the superior engaging surface 103, which is the superior inner wall of the suction ring, engages the corneal region. The engaged corneal region is the cornea and one portion of the limbo, the zone that joins the cornea and the conjunctiva. When suction is applied to the annular vacuum channel 102, the ocular globe is slightly drawn into the annular vacuum channel, or "pinched", creating a seal and firmly gripping and immobilizing the eye in relation to the microkeratome. FIG. 7A is a cross-sectional side view showing an eye 108 inserted into a suction ring 100 and FIG. 7B is a cross-sectional side view showing the effect on the eye of the suction introduced to the annular vacuum channel, "pinching" the ocular globe to hold it securely in place in relation to the microkeratome.

If the suction ring engaging surfaces do not have approximately the same dimensions in all directions as the ocular globe being engaged, then there is a high risk of losing the suction seal during the lamellar keratotomy. To overcome this problem in the past, physicians have increased the suction pressure to pull the ocular globe against the sealing surfaces. Using the higher suction, however, increases the intraocular pressure placing eye structures, such as the retina, at risk. In accordance with the present invention, by changing the shape of the suction ring engaging surfaces to better match the shape of the ocular globe and corneal region, a lower suction pressure can be used reliably to securely engage the suction ring to the ocular globe and corneal region, thereby avoiding the risks associated with higher intraocular pressure.

Two meridians, a–a' and b–b' intersecting at ninety degrees, may be used to describe the shape of an ocular globe and its cornea. As the difference in the length of the radius for the two meridians increases, the ocular globe and the cornea becomes more aspherical, causing astigmatism. The majority of refractive surgery cases have an astigmatic cornea of less than 2 diopters between one meridian and the other. However, when the astigmatic cornea is greater than 2 diopters between the meridians, or the difference in radii between one meridian and the other is greater than about 1 mm, the present invention has been found to maintain a suction seal without the use of higher suction pressure.

Figures 2, 8A:
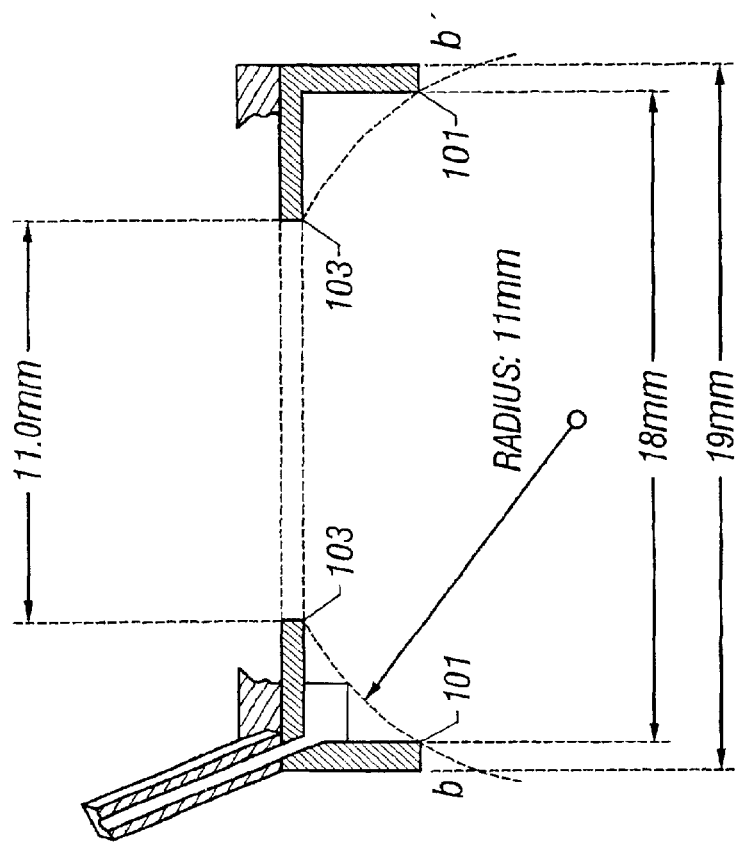
Figures 1, 8A:
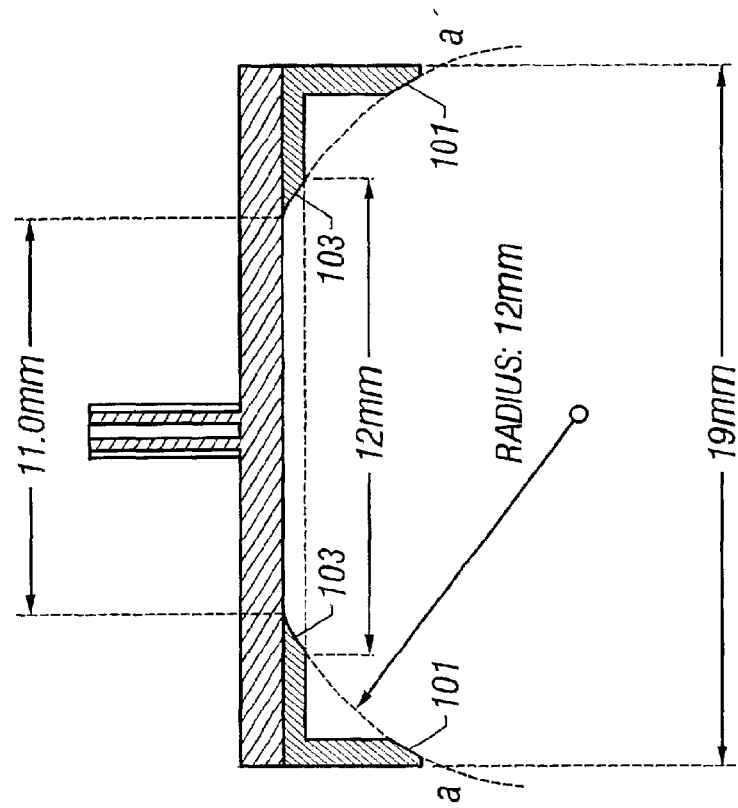

The present invention provides a suction ring having a gripping or engaging structure shaped to provide a closer fit to the non-circular plane section of astigmatic ocular globes and corneal regions, thereby reducing the need to increase the suction pressure to achieve an adequate suction seal. The inferior end of the suction ring has an inner diameter and an outer diameter describing the inner and outer walls, the difference in these diameters being the thickness of the suction ring. The inner wall is the inferior engaging surface that grips the sclera. FIG. 8A shows the preferred embodiment of the invention providing an inferior engaging surface 101 having a non-circular plane section (e.g., ovoid, elliptical, oval) for gripping a sclera having a similar non-circular plane section. In this example, the a–a' meridian radius of the ocular globe is 12 mm and the b–b' meridian radius is 11 mm. By beveling the inner wall of a suction ring having a circular outer wall, such that the radii of the meridians of the inferior engaging surface 101 closely match the radii of the meridians of the ocular glove, the diameter of the inferior engaging surface can vary, for example, from a maximum of 19 mm at the engagement along the a–a' meridian down to 18 mm at the engagement along the b–b' meridian, providing a close fit between the inferior engaging surface and the aspherical ocular globe.

Figures 2, 8B:
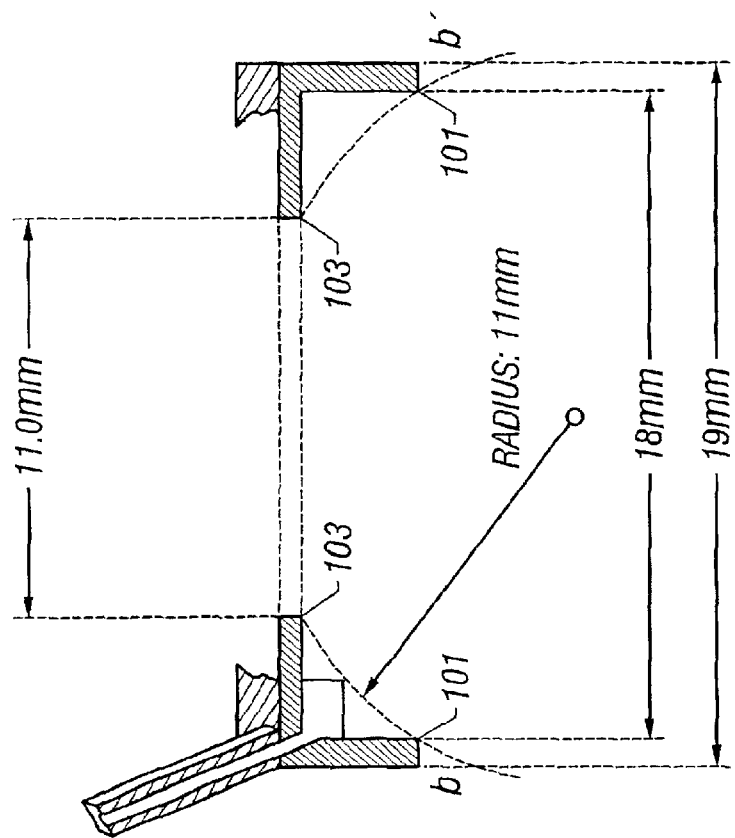
Figures 1, 8B:
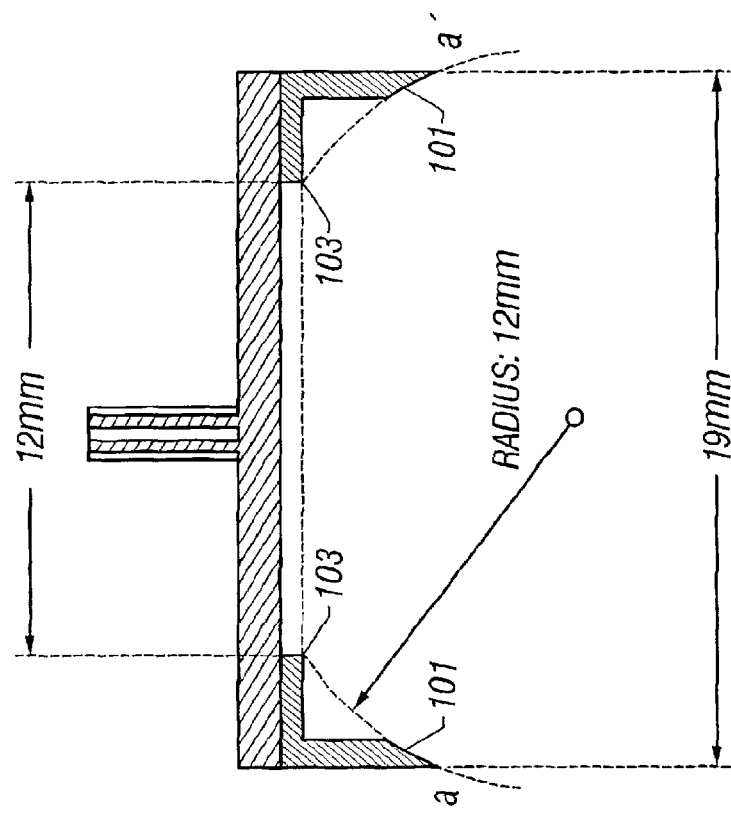
Figures 1, 8C:
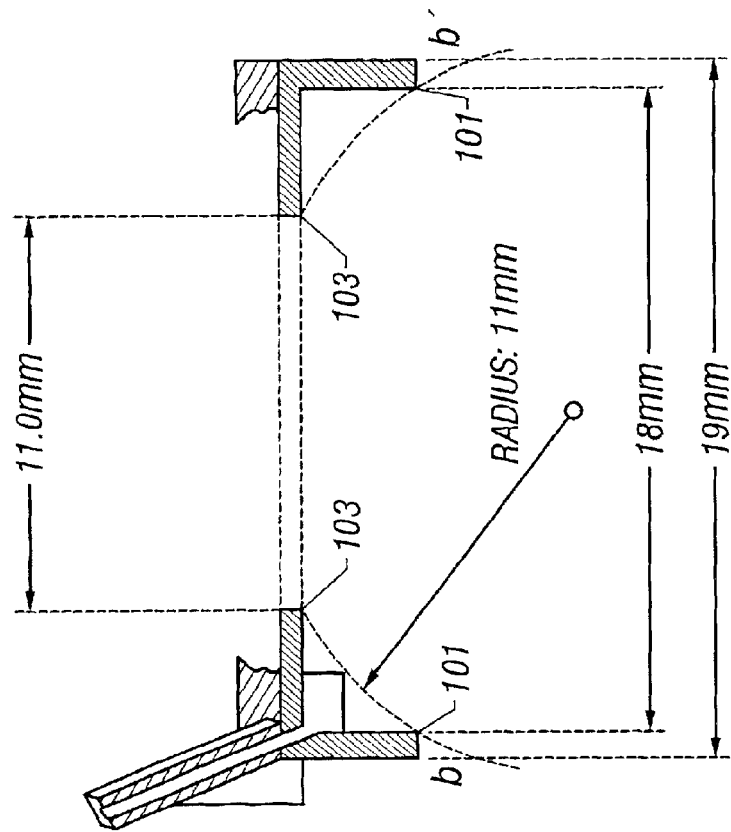
Figures 2, 8C:
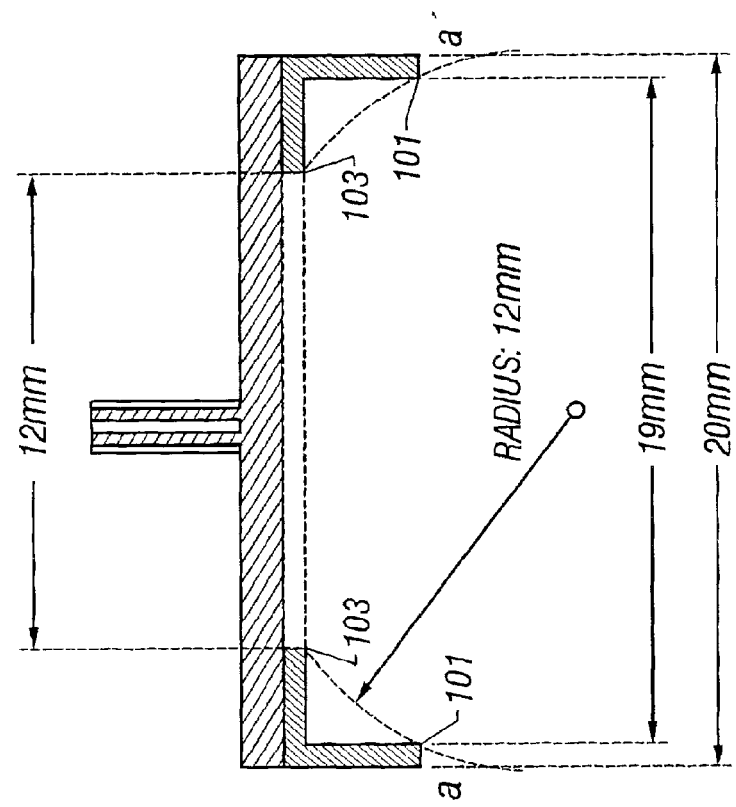

Alternatively, as shown in FIG. 8C, the inferior engaging surface 101 of the suction ring could be formed in a non-circular shape, having an equal suction ring thickness around the circumference of the inferior engaging surface, i.e., not beveled, while still providing a close fit between the inferior engaging surface and the aspherical ocular globe.

The superior end of the suction ring also has an inner diameter and an outer diameter describing the inner and outer walls, the difference in these diameters being the thickness of the suction ring. The inner wall is the superior engaging surface that grips the corneal region. FIG. 8A shows the preferred embodiment of the invention providing a superior engaging surface 103 having a non-circular plane section (e.g., ovoid, elliptical, oval) for gripping the corneal region having a similar non-circular plane section. In this example, the a–a' meridian radius of the ocular globe is 12 mm and the b–b' meridian radius is 11 mm. By circular outer wall, such that the radii of the meridians of the superior engaging surface closely match the radii of the meridians of the corneal region, the diameter of the superior engaging surface can vary from a maximum of 19 mm at the engagement along the a–a' meridian down to 18 mm at the engagement along the b–b' meridian, providing a close fit between the superior engaging surface and the astigmatic corneal region. In this example, the diameter of the aperture is 11 mm along both meridians resulting in a circular corneal disk cut.

Alternatively, as shown in FIG. 8B, the superior engaging surface 103 of the suction ring could be formed in a non-circular shape, having an equal suction ring thickness around the circumference of the superior engaging surface, i.e., not beveled, while still providing a close fit between the superior engaging surface and the astigmatic corneal region. For the example shown in FIG. 8B, the diameter of the aperture is 12 mm along the a–a' meridian and 11 mm along the b–b' meridian allowing an oval corneal disk to be cut.

Figures 2, 8D:
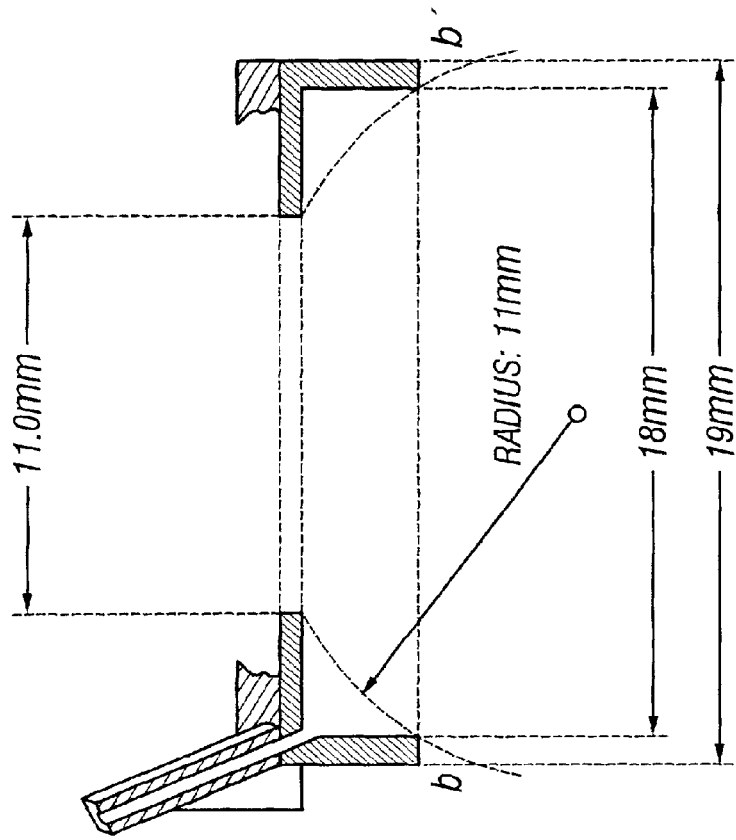
Figures 1, 8D:
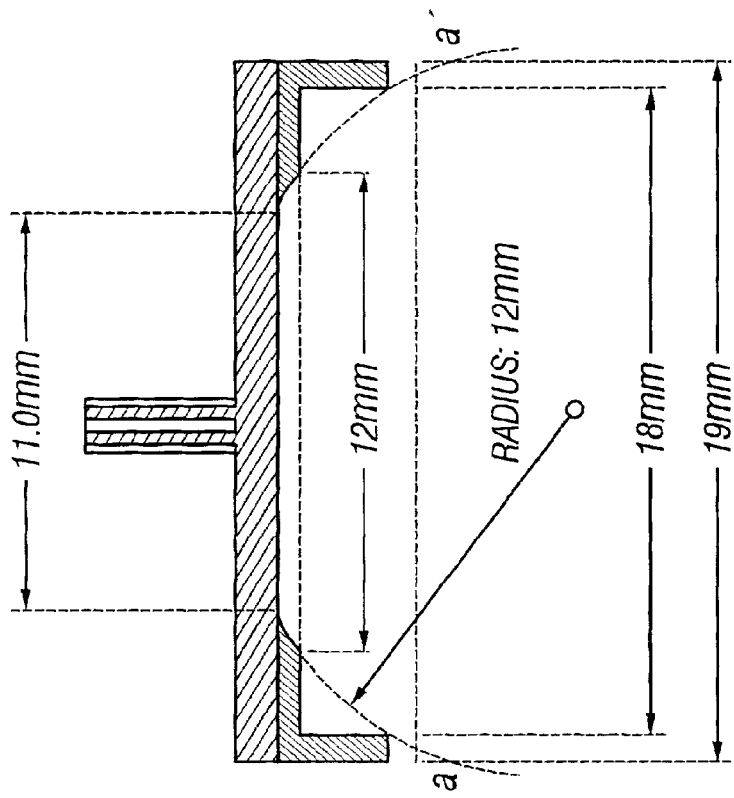

Optionally, as shown in FIG. 8D, the inferior engaging surface 101 of the suction ring could be formed to provide a close non-circular fit between the engaging surface and the non-circular plane section of the ocular globe by varying the height of the suction channel 102. In the example of FIG. 8D, the a–a' meridian radius of the ocular globe is 12 mm and the b–b' meridian radius is 11 mm. By reducing the length of the suction channel 102 wall along the a–a' meridian, the inferior engaging surface will grip the ocular globe closer to the corneal region where the distance across the eyeball is 18 mm. Along the b–b' meridian, the inferior engaging surface will grip the ocular globe further from the corneal region where the distance across the eyeball is also 18 mm. The height of the suction chamber inferior wall between the meridians will vary smoothly from the height at the first meridian to the height at the adjacent meridian to ensure a close fit between the inferior engaging surface and the sclera. In this example, the diameter of the aperture is 11 mm for both meridians resulting in a circular corneal disk cut.

The examples shown in FIGS. 8A through 8D can be varied in many ways, with suction rings so dimensioned that the superior and inferior engaging surfaces closely fit ocular globes having different aspherical dimensions and astigmatic corneal regions. While these examples describe suction rings having radii of these engaging surfaces differing for only the two main meridians, the radii of the engaging surfaces could also be varied for more than two meridians. The engaging surfaces between meridians will preferably have a smooth gradual change from the diameter of one meridian to the diameter of an adjacent meridian.

It should be recognized that changes could be made to the diameters of the inferior and superior engaging surfaces without affecting the diameter of the aperture through which the cornea is presented for the lamellar keratotomy or other corneal surgical procedure. Similarly, the diameter of the aperture can be varied without affecting the diameter of the superior and inferior engaging surfaces. Furthermore, the shape of the aperture can be round, oval, or other non-circular shape allowing the physician to cut a corneal disk in a shape other than a circle.

It is an advantage that non-circular corneal disks may be obtained with the present invention. When the cornea is extended into the top aperture of the suction ring, the flatter meridian tends to curve and the more curved meridian tends to flatten to conform to the aperture of the suction ring. The suction produced by the vacuum pump helps the cornea to adjust and fit into the aperture. If the aperture is circular, the corneal section protruding through the aperture becomes basically circular and when cut with the microkeratome, the resulting corneal disk is circular. If the aperture is non-circular, e.g., oval, elliptical or ovoid, then the corneal section protruding through the aperture will basically assume that shape and when cut with a microkeratome, the resulting corneal disk will be the non-circular shape.

Figure 9A:
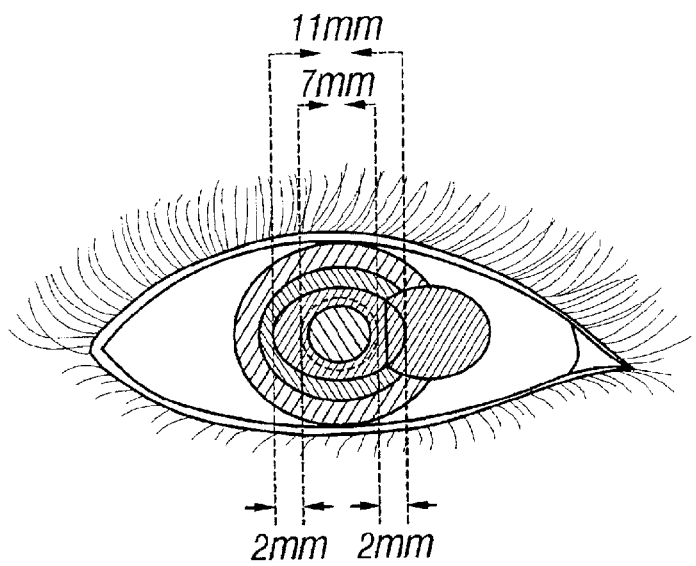
FIG. 9A shows an oval corneal disk for a myopic ablation zone.
Figure 9B:
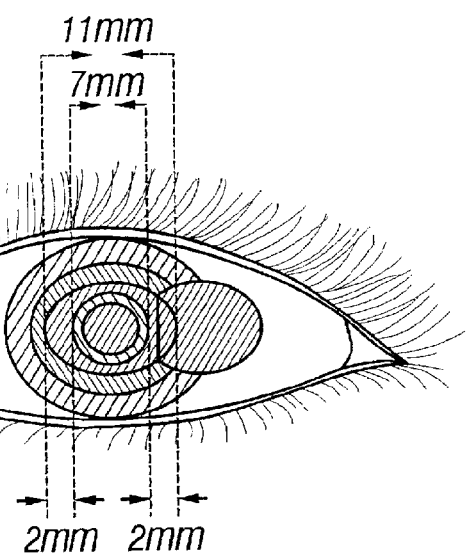
FIG. 9B shows an oval corneal disk for a hyperopic ablation zone.
Figure 9C:
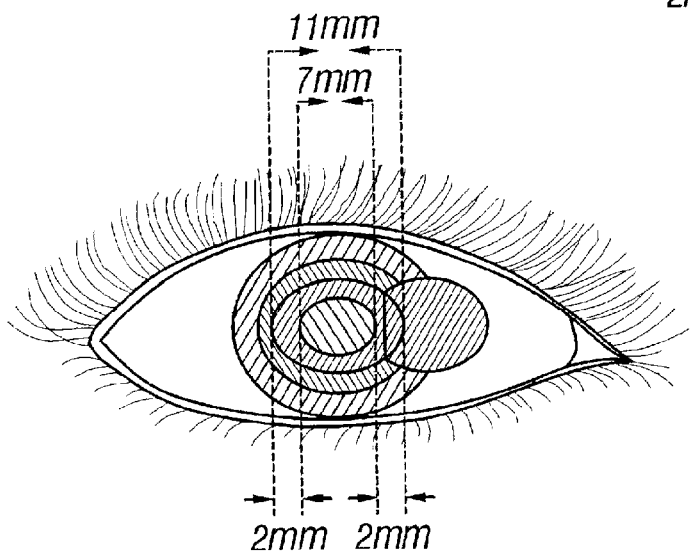
FIG. 9C shows an oval corneal disk for an astigmatic ablation zone.

Using a corneal disk having an elliptical or other non-circular shape, the area of the ablation zone may be better exposed for laser resection without the concern of negative hinge syndrome, which is the accidental ablation of the hinge. FIGS. 9A, 9B, and 9C show oval corneal disks 11 that could be obtained using the present invention during lamellar keratotomy. These figures show, respectively, a myopic 20, a hyperopic 21 and an astigmatic 22 ablation zone. By obtaining an oval corneal disk, more stromal tissue is exposed for ablation while minimizing the total stromal tissue exposed. Furthermore, obtaining an oval corneal disk exposes a greater area of stromal tissue for ablation without having to use a larger diameter suction ring with the inherent risk caused by the higher suction requirements to grip the ocular globe.

The present invention suction ring can be used with other instruments for corneal surgical procedures requiring the ocular globe to be immobile in relation to the surgical instruments. These surgical instruments may be, for example, microkeratomes, various scalpels or incisors, corneal markers, artificial chambers and corneal dissectors. A specific example of a suitable microkeratome can be found in U.S. Pat. No. 5,980,543 to Carriazo et al., the entirety of which is herein incorporated by reference. Embodiments of the ring of the present invention are suitable for use with microkeratomes having pendular as well as horizontal cutting paths. The ring may be made from stainless steel, titanium, a synthetic plastic, rubber and combinations thereof.

The present invention may further be applied to advantage in the form of a kit for use with a microkeratome having a cutting head assembly. The kit comprises a plurality of rings for securing aspherical ocular globes, and each of the plurality of rings has: (1) an aperature sized to receive and expose a cornea; (2) a fixed dimension interface for interfacing with the cutting head assembly; and (3) and annular vacuum channel that is connectable to a vacuum source. The annular vacuum channel has an aspherical ocular globe-engaging surface comprising an inferior engaging surface and a superior engaging surface. Two or more of the rings of the kit differ in a manner selected form aperture dimension or shape, superior engaging surface dimension or shape, inferior engaging surface dimension or shape, and combinations thereof.

While the foregoing is directed to the preferred embodiment of the present invention, other and further embodiments of the invention may be devised without departing from the basic scope thereof, and the scope thereof is determined by the claims that follow.

What is claimed is:

1. An apparatus for securing an aspherical ocular globe, comprising:
   a ring having an annular vacuum channel that is connectable to a vacuum source and an aperture sized to receive and expose the cornea;

wherein the annular vacuum channel has an aspherical inferior engaging surface and an aspherical superior engaging surface.

2. The apparatus of claim 1, wherein the aperture is non-circular.

3. The apparatus of claim 1, wherein the aperture is a shape selected from the group consisting of circular, elliptical, oval and ovoid.

4. The apparatus of claim 1, wherein the inferior engaging surface and the superior engaging surface are defined by a major meridian and a minor meridian having different radii.

5. The apparatus of claim 1, wherein the inferior engaging surface and the superior engaging surface are defined by a plurality of meridians having different radii.

6. The apparatus of claim 1, wherein the inferior engaging surface has a non-circular plane section that is formed by a non-circular wall, a beveled wall, or a variable length wall.

7. The apparatus of claim 1, wherein the superior engaging surface has a non-circular plane section that is formed by a non-circular wall or a beveled wall.

8. The apparatus of claim 1, wherein the inferior and superior engaging surfaces each has a shape selected from the group consisting of elliptical, oval, ovoid, and combinations thereof.

9. The apparatus of claim 1, wherein the inferior and superior engaging surfaces each has one or more concave surfaces that mate with a convex surface of the ocular globe and corneal region.

10. The apparatus of claim 1, wherein the ring is made from a material selected from stainless steel, titanium, a synthetic plastic, rubber, and combinations thereof.

11. A kit for use with a microkeratome having a cutting head assembly, comprising:

a plurality of rings for securing aspherical ocular globes, wherein each of the plurality of rings has:

(1) an aperture sized to receive and expose a cornea, (2) a fixed dimension interface for interfacing with the cutting head assembly, (3) an annular vacuum channel that is connectable to a vacuum source, wherein the annular vacuum channel has an aspherical inferior engaging surface and an aspherical superior engaging surface, wherein two or more of the rings differ in a manner selected from aperture dimension or shape, superior engaging surface dimension or shape, inferior engaging surface dimension or shape, and combinations thereof.

12. The kit of claim 11, wherein the aperture is non-circular.

13. The kit of claim 11, wherein the aperture is a shape selected from the group consisting of circular, elliptical, oval and ovoid.

14. The kit of claim 11, wherein the inferior engaging surface and the superior engaging surface are defined by a major meridian and a minor meridian having different radii.

15. The kit of claim 11, wherein the inferior engaging surface and the superior engaging surface are defined by a plurality of meridians having different radii.

16. The kit of claim 11, wherein the inferior engaging surface has a non-circular plane section that is formed by a non-circular wall, a beveled wall or a variable length wall.

17. The kit of claim 11, wherein the inferior engaging surface has a non-circular plane section that is formed by a wall or a beveled wall.

18. The kit of claim 11, wherein the inferior and superior engaging surfaces each has a shape selected from the group consisting of elliptical, oval, ovoid and combinations thereof.

19. The kit of claim 11, wherein the inferior and superior engaging surfaces each has one or more concave surfaces that mate with a convex surface of the ocular globe and corneal region.

20. The kit of claim 11, wherein the plurality of suction rings are made from a material selected from stainless steel, titanium, a synthetic plastic, rubber, and combinations thereof.

21. A microkeratome for performing a lamellar keratotomy of an aspherical ocular globe, comprising:

a ring having an annular vacuum channel that is connectable to a vacuum source, an aperture sized to receive and expose the cornea, and an interface, wherein the annular vacuum channel has an aspherical ocular globe engaging surface comprising an inferior engaging surface and an aspherical superior engaging surface;

a blade suitable for corneal resections;

a cutting head for carrying the blade over the guide ring through a cutting path defined by the guide ring;

an adjustable cornea compression device connected to the cutting head for at least partially compressing the cornea ahead of the blade so as to set the corneal resection to a desired shape and thickness;

means for driving the cutting head and the cornea compression device across the guide ring.

22. The microkeratome of claim 21, wherein the aperture is non-circular.

23. The microkeratome of claim 21, wherein the aperture is a shape selected from the group consisting of circular, elliptical, oval and ovoid.

24. The microkeratome of claim 21, wherein the inferior engaging surface and the superior engaging surface are defined by a major meridian and a minor meridian having different radii.

25. The microkeratome of claim 21, wherein the inferior engaging surface and the superior engaging surface are defined by a plurality of meridians having different radii.

26. The microkeratome of claim 21, wherein the inferior engaging surface has a non-circular plane section that is formed by a wall, a beveled wall or a variable length wall.

27. The microkeratome of claim 21, wherein the superior engaging surface has a non-circular plane section that is formed by a wall or a beveled wall.

28. The microkeratome of claim 21, wherein the inferior and superior engaging surfaces each has a shape selected from the group consisting of elliptical, oval, ovoid and combinations thereof.

29. The microkeratome of claim 21, wherein the inferior and superior engaging surfaces each has one or more concave surfaces that mate with a convex surface of the ocular globe and corneal region.

30. The microkeratome of claim 21, wherein the aspherical ocular globe-engaging surface is suitable for contacting an ocular globe and corneal region having a refractive error selected from astigmatism, hyperopia and myopia.

31. The microkeratome of claim 21, wherein the cutting path is horizontal.

32. The microkeratome of claim 21, wherein the cutting path is pendular.

* * * * *